United States Patent [19]

Böck et al.

[11] Patent Number: 5,019,514
[45] Date of Patent: May 28, 1991

[54] *AUREOBASIDIUM PULLULANS* STRAIN, PROCESS FOR ITS PREPARATION, AND USE THEREOF

[75] Inventors: August Böck, Geltendorf; Konrad Lechner; Otto Huber, both of Munich, all of Fed. Rep. of Germany

[73] Assignee: Consortium fur elektrochemische Industrie GmbH, Munich, Fed. Rep. of Germany

[21] Appl. No.: 471,112

[22] Filed: Nov. 27, 1989

Related U.S. Application Data

[63] Continuation of Ser. No. 925,708, Oct. 30, 1986, abandoned.

[30] Foreign Application Priority Data

Nov. 5, 1985 [DE] Fed. Rep. of Germany ....... 3539180

[51] Int. Cl.⁵ .............................................. C12N 1/14
[52] U.S. Cl. ..................................... 435/254; 435/911

[56] References Cited

U.S. PATENT DOCUMENTS 4,309,505  1/1982  Smith et al. .................... 425/911

OTHER PUBLICATIONS

Chemical Abstracts, CA 100(3):19055b, p. 184, Jan. 16, 1984, Arnaud et al., "Mutagenic Action of N-Nitroso-N-Methylbiuret on *Aureobasidium pullulans*".
Chemical Abstracts 98: 67978s, p. 284, Feb. 1983, Elinov, N. P. et al., "Mutability of *Aureobasidium pullulans* (D. By.) Induced by UV Light and Mitomycin C."
Chemical Abstracts 88: 34389r, p. 239, Jan. 1978, Kelley, P. J. et al., "The Effect of Ethidium Bromide Mutagenesis on Dimorphism, Extracellular Metabolism and Cytochrome Levels in *Aureobasidium pullulans*."

*Primary Examiner*—Douglas W. Robinson
*Assistant Examiner*—Marian C. Knode
*Attorney, Agent, or Firm*—Collard, Roe & Galgano

[57] ABSTRACT

The invention relates to *Aureobasidium pullulans* strains which produce pullulan but virtually no melanin. A process for the preparation of these strains, and a preferred use, are also disclosed.

1 Claim, No Drawings

AUREOBASIDIUM PULLULANS STRAIN, PROCESS FOR ITS PREPARATION, AND USE THEREOF

CROSS REFERENCE TO RELATED APPLICATION

This is a continuation application of prior copending U.S. Pat. application Ser. No. 925,708, filed Oct. 30, 1986, and now abandoned.

The invention relates to an *Aureobasidium pullulans* strain which produces pullulan but virtually no melanin, and to a process for the preparation thereof and to the use thereof.

It is known that strains of the genus Aureobasidium produce pullulan. Pullulan is a polysaccharide having maltotriose units (alphal—4 bonds) which are linked as follows: alphal—6; compare Bernier in *Can. J. Microbiol.*, 4 (1958) 195-204, and Bender, Lehnmann & Wallenfels in *Biochem. Biophys. Acta*, 36 (1959) 309-316.

The polysaccharide pullulan has a variety of uses, for example:

(1) for the preparation of transparent films which are permeable to carbon dioxide but not to oxygen;
(2) as a flocculating agent; and
(3) as a substitute for dextran in infusion fluids.

Strains of the genus Aureobasidium form a greenish black pigment (melanin) during cultivation. This melanin cannot be removed with the conventional extraction of pullulan.

Accordingly, it is an object of the present invention to provide *Aureobasidium pullulans* strains which produce melanin to a lesser extent than those known to the state of the art.

A further object of the present invention is to provide a process for the preparation of strains of this type, and the use of these strains for the preparation of pullulan.

The foregoing and related objects are attained by the present invention which relates to an *Aureobasidium pullulans* strain which produces pullulan, but with a reduced level of melanin as compared to such strains presently known, and which can be obtained by:

(a) exposing an A. pullulans strain which produces pullulan and melanin to mutating conditions in a known manner;
(b) cultivating, in a known manner, the strain which has been exposed to the mutating conditions; and
(c) selecting a mutated *A. pullulans* strain (in the form of one or more colonies), and strains derived therefrom, the pigmentation of the selected strain and the derived strains being less than that of the initial strain or zero.

The mutated strain can be cultivated on, for example, an agar plate culture medium. The selected colonies can be tested in liquid culture to determine whether they still produce satisfactory yields of pullulan.

*A. pullulans* strains, according to the invention, can be obtained by mutation by irradiation with UV light or chemical treatment, in particular by treatment with ethyl methanesulfonate.

The formation of melanin takes some time. In order to be able to assess the formation of melanin, or the absence of the formation of melanin, in cultures, it is advantageous for the individual colonies not to be grown together so that the formation of a cell lawn is prevented. For this purpose, it is possible to carry out the cultivation stage of the invention (i.e., stage (b)), in a temperature range at which little or no cell multiplication would occur, but which still would support the formation of melanin. In particular, the temperature should be in the range of from 2° to 13° C. and, preferably, 4° to 10° C.

It is possible to use ATCC 9348 as the initial strain. One mutation product of this known strain is the *A. pullulans* strain P 56 which has been deposited at the following depository authority and has received the following deposition number: Deutsche Sammlung für Mikroorganismen (German collection of microorganisms) DSM 3562. The mycology of P 56 differs from that of ATCC 9348 in that the strain according to the invention does not form melanin and, further, the formation of pullulan is higher than that of the initial strain by 50% and more.

*A. pullulans* strains according to the invention can be prepared by carrying out the above-mentioned stages (a) to (c), where appropriate, with the more specific measures mentioned above.

Pullulan can be obtained by cultivation of an *A. pullulans* strain, according to the invention, in a culture medium, allowing the pullulan to be produced, and removing the formed pullulan from the culture medium. The culture medium ought to contain carbon sources which the strain can utilize (for example, glucose, sucrose, maltose or xylose among other sources) as well as yeast extract and inorganic salts essential for cell growth. Normally, the cultivation is carried out under aerobic conditions as a shake culture or submerged culture with aeration at a temperature of, for example, 20° to 30° C. and a pH of, for example, 2.5 to 6.

The invention will now be explained more fully in a number of examples which are, however, only given by way of illustration and not of limitation.

Example 1

A commercially available *A. pullulans* strain (for example, ATCC 9348) is cultivated in a Le Duy culture medium containing 5 g/l $K_2HPO_4$, 1 g/l NaCl, 0.6 g/l $(NH_4)_2SO_4$, 0.2 g/l $MgSO_4, 7H_2O$, 0.4 g/l yeast extract and 30 g/l sucrose, the pH being adjusted to 5.5 with HCl.

The strain is cultivated in this medium for 24 hours. The mycelium is then removed by centrifugation at 6,000× g for 5 min. The supernatant is recentrifuged at 17,000× g for 10 min. The pellets resulting from the centrifugation are washed with physiological saline solution, and then the cell density is adjusted to $1 \times 10^7$ cells/ml. The suspension is then irradiated with UV light (354 nm; 1,400 $\mu W/cm^2$) for 7 to 8 min.

The suspension (0.1 ml) is plated onto an agar culture plate (extract of 300 g of potatoes, 20 g of glucose and 15 g of agar/l) for 2 to 3 days. The plates are left to stand at 4° C. for 8 days. Then unpigmented and virtually unpigmented colonies are selected. The selected colonies are checked for whether they still produce satisfactory amounts of pullulan.

Example 2

A culture medium is prepared with the following ingredients: 1 l of distilled water, 5 g of $K_2HPO_4$, 1 g of NaCl, 0.6 g of $(NH_4)_2SO_4$, 0.2 g of $MgSO_4 \times 7H_2O$, 0.4 g of yeast extract and 30 g of carbon sources (see above).

100 ml of the culture medium are adjusted to a pH of 5.5 with HCl.

The culture medium is then placed in a 500 ml Erlenmeyer flask and is sterilized. The culture medium is then inoculated with the strain P 56, according to the invention, which has been prepared as in Example 1. Cultivation is carried out at 26° C. with shaking (200 rpm).

After cultivation for 7 days, the culture is centrifuged at 27,000× g for 15 min. Twice the volume of 96% ethanol is added to and mixed with the supernatant; the mixture is recentrifuged at 1000× g for 10 min, during which white pullulan separates out. The collected product is washed, milled, redissolved in water, reprecipitated with ethanol, and then dried.

To check the identity, the resulting product can be subjected to $^{13}C$ NMR analysis and high performance liquid chromatography (HPLC).

Comparison Example 1

Example 2 is repeated but with the exception that a commercially available *A. pullulans* strain (for example ATCC 9348) is used. The resulting pullulan has an intense greenish black coloration.

While only several embodiments and examples of the present invention have been described, it is obvious that many changes and modifications may be made thereunto, without departing from the spirit and scope of the invention.

What is claimed is:

1. A culture of *Aureobasidium pullulans* strain P 56, or strains derived therefrom, which produce pullulan and have a lower quantity level of melanin than *Aureobasidium pullulans* ATCC 9348.

* * * * *